United States Patent
Rao

[11] Patent Number: 6,165,931
[45] Date of Patent: Dec. 26, 2000

[54] CATALYTIC HYDROFLUORINATION PROCESSES AND CATALYSTS

[75] Inventor: V. N. Mallikarjuna Rao, Wilmington, Del.

[73] Assignee: E. I. du Pont de Nemours and Company, Wilmington, Del.

[21] Appl. No.: 08/825,173

[22] Filed: Apr. 11, 1997

Related U.S. Application Data

[60] Provisional application No. 60/015,779, Apr. 16, 1996.

[51] Int. Cl.[7] .......................... B01J 27/08; B01J 27/138; B01J 27/128; B01J 23/10
[52] U.S. Cl. ........................ 502/224; 502/226; 502/228; 502/229; 502/302; 502/303; 502/439; 570/164; 570/165; 570/166; 570/168; 570/169; 570/170
[58] Field of Search .................................... 502/224, 226, 502/228, 229, 302, 303, 439; 570/164, 165, 166, 168, 169, 170

[56] References Cited

U.S. PATENT DOCUMENTS

| | | | |
|---|---|---|---|
| 3,231,519 | 1/1966 | Clark et al. | |
| 3,900,429 | 8/1975 | Komatsu et al. | 423/213.5 |
| 4,535,067 | 8/1985 | Courty et al. | 502/84 |
| 5,693,588 | 12/1997 | Poston | 502/400 |

FOREIGN PATENT DOCUMENTS 0 518 506 A2  12/1992  European Pat. Off. .

OTHER PUBLICATIONS

L.E. Manzer et al., *Advanced Cat.*, 39, 329–350, 1993, No Month Available.
M. Bannert et al., Reactions of Lanthanum Fluoride With Haloalkanes, *Z. Anorg. Allg. Chem*, 421, 135–142, 1996, No Month Available.

*Primary Examiner*—Elizabeth D. Wood

[57] ABSTRACT

A process is disclosed for increasing the fluorine content of a saturated or olefinic halogenated hydrocarbon starting material of the formula $C_nH_aCl_bF_c$, wherein n is an integer from 1 to 6, a is an integer from 0 to to 12, b is an integer from 0 to 13 and c is an integer from 0 to 13. The process involves contacting the starting material in the vapor phase at a temperature in the range of about 150° C. to about 500° C. with HF and a catalytic metal supported on a trivalent lanthanum compound support (the catalytic metal being chromium, cobalt, nickel, zinc, magnesium, copper, silver and/or gold). Certain catalytic compositions including catalytic metal (e.g., chromium, nickel, cobalt, zinc and/or magnesium) supported on a support at trivalent lanthanum compound containing fluoride anion are also disclosed. The atomic ratio of catalytic metal to lanthanum in the compositions is from about 1:1 to 1:999.

15 Claims, No Drawings

CATALYTIC HYDROFLUORINATION PROCESSES AND CATALYSTS

This application claims the priority benefit of U.S. Provisional Application Ser. No. 60/015,779, filed Apr. 16, 1996.

FIELD OF THE INVENTION

This invention relates to processes for the manufacture of saturated halohydrocarbons containing fluorine, and more particularly to vapor phase catalytic processes for producing chlorofluorocarbons as intermediates, hydrochlorofluorocarbons and hydrofluorocarbons using supported catalysts.

BACKGROUND

A number of chlorine-containing halocarbons are considered to be detrimental toward the Earth's ozone layer. There is a world-wide effort to develop materials having lower ozone depletion potential that can serve as effective replacements. For example, the hydrofluorocarbon, 1,1,1,2-tetrafluoroethane (HFC-134a) is being used as a replacement for dichlorodifluoromethane (CFC-12) in refrigeration systems. There is a need for manufacturing processes that provide fluorocarbons that contain less chlorine or no chlorine.

Numerous processes have been developed for changing the fluorine content of halogenated hydrocarbons. Various catalysts have been proposed for use in facilitating processes such as hydrofluorination. See, e.g., L. E. Manzer et al., Adv. Catal. (39) pp. 329–350 (1993). The catalysts proposed for use include catalysts involving one or more catalytic metals on a selected support. For example, a well known class of catalysts includes metals supported on alumina or fluorinated alumina. M. Bannert et al., Z. Anorg. Allg. Chem. 421, 135–142 (1976) report the use of lanthanum fluoride. U.S. Pat. No. 3,231,519 discloses halogen exchange catalyst consisting essentially of iron oxide, didymium oxide (which can contain $La_2O_3$) and zirconium oxide. There is an interest in developing additional catalysts which can be effectively used for changing the fluorine content of halogenated hydrocarbons.

SUMMARY OF THE INVENTION

This invention provides a process for increasing the fluorine content of a saturated or olefinic halogenated hydrocarbon starting material of the formula $C_nH_aCl_bF_c$, wherein n is an integer from 1 to 6, a is an integer from 0 to to 12, b is an integer from 0 to 13 and c is an integer from 0 to 13. The process is characterized by contacting said starting material in the vapor phase at a temperature in the range of about 150° C. to about 500° C. with HF and a catalytic metal supported on a trivalent lanthanum compound support, said catalytic metal being selected from the group consisting of chromium, cobalt, nickel, zinc, magnesium, copper, silver and gold and mixtures thereof This invention also provides a catalytic composition comprising at least one catalytic metal selected from the group consisting of chromium, nickel, cobalt, zinc and magnesium supported on a support at trivalent lanthanum compound containing fluoride anion; the atomic ratio of catalytic metal to lanthanum being from about 1:1 to 1:999.

DETAILED DESCRIPTION

The catalysts of use for this invention include metal compounds on lanthanum oxide; metal compounds on lanthanum fluoride; and metal compounds on fluorided lanthanum oxide. By fluorided lanthanum oxide is meant a composition comprising lanthanum, oxygen and fluorine in which the fluorine content has been enriched by fluorinating an oxide of lanthanum. Preferably, the lanthanum, oxygen and fluorine are present in the fluorinated lanthanum oxide in such proportions that the fluorine content corresponds to a $LaF_3$ content of at least 80 weight percent of the catalyst composition, exclusive of the supported metal compound(s) present. Except when the $LaF_3$ content is 100%, the composition can include lanthanum oxide and lanthanum oxyfluorides (e.g., LaOF). Of note is a support of fluorided lanthanum oxide consisting essentially of lanthanum, oxygen and fluorine in such proportions that the fluorine content corresponds to a $LaF_3$ content of at least 80% by weight of the catalyst composition, exclusive of the supported metal compound(s) present, said fluorine content being obtained by pretreatment of an unfluorinated catalyst with a vaporizable fluorine-containing compound.

Fluorided lanthanum oxide compositions can be prepared in any manner known to the art for the preparation of fluorided alumina. For example, the catalyst composition can be prepared by fluorination of lanthanum oxide impregnated with a solution of catalytic metal(s) (e.g., at least one chromium, nickel, manganese, zinc or cobalt compound) which may be in the form of the oxide, oxyhalide, halide, nitrate, sulfate or other compound of the metal. The halides include fluorides, chlorides and bromides.

The catalyst composition can also be prepared by co-precipitation of the catalytic metal and the lanthanum as the hydroxides which are thereafter dried and calcined to form the mixed oxides, a technique well known to the art. The resulting oxide can then be pretreated as described herein.

The total content of catalytic metal (e.g., chromium, nickel, zinc, cobalt or magnesium) expressed as metal is typically not more than 50% by weight of the catalyst composition, and is preferably not more than 30% by weight of the catalyst composition; and is usually at least about 0.05% by weight of the catalyst composition, and is preferably at least about 0.1% by weight of the catalyst composition. A particularly preferred range is from 0.1 to 10% by weight of the catalyst composition. Preferably, the catalytic metals are present as halides, oxyhalides including mixed halides and oxyhalides such as metal chlorofluorides, and oxides. The preferred catalytic metals include chromium, nickel, zinc, cobalt and magnesium. Chromium is especially preferred.

The unfluorinated catalyst composition can be fluorinated to the desired fluorine content by treating with a fluorine-containing compound at elevated temperatures, e.g., at about 200° C. to about 450° C. The pretreatment with a vaporizable fluorine-containing compound such as HF, $SF_4$, $CCl_3F$, $CCl_2F_2$, $CHF_3$, $CHClF_2$ or $CCl_2FCClF_2$ can be done in any convenient manner including in the reactor which is to be used for contacting the halogenated hydrocarbon starting material with HF. By vaporizable fluorine-containing compound is meant a fluorine-containing compound which, when passed over the catalyst at the indicated conditions, will fluorinate the catalyst to the desired degree.

A suitable catalyst may be prepared, for example, as follows:

A quantity of $La_2O_3$ is impregnated with a solution, usually aqueous, of a catalytically effective amount of one or more of the metal compounds described above (e.g., chromium, cobalt, nickel, zinc and/or magnesium halides).

By catalytically effective amount is meant an amount of the metal which causes the production of the desired compounds in the process of the instant invention. Normally, this amount, expressed as metal, will be between about 0.05 to 50 weight percent of the lanthanum oxide support, preferably not more than 30 weight percent, and more preferably 0.1 to 10 weight percent. The impregnated $La_2O_3$ can be dried until essentially all moisture is removed, e.g., for about 18 hours at about 400° C. The dried catalyst is then transferred to the reactor to be used. The temperature is then gradually increased to about 400° C. while maintaining a flow of $N_2$ through the reactor to remove any remaining traces of moisture from the catalyst and the reactor. The temperature is then lowered to about 200° C. and HF, or other vaporizable fluorine containing compounds such as HF, $SF_4$, $CCl_3F$, $CCl_2F_2$, $CHF_3$, $CHClF_2$ or $CCl_2FCClF_2$, diluted with $N_2$ passed through the reactor. The $N_2$ can be gradually reduced until only HF, or other vaporizable fluorine-containing compounds such as $SF_4$, $CCl_3F$, $CCl_2F_2$, $CHF_3$, $CHClF_2$ or $CCl_2FCClF_2$, is being passed through the reactor. At this point the temperature can be increased to about 450° C. and held at that temperature to convert the impregnated $La_2O_3$ to a fluorine content corresponding to at least 80% $LaF_3$ by weight, e.g., for 15 to 300 minutes, depending on the flow of the fluorine containing compound and the catalyst volume.

Another suitable procedure for the catalyst preparation is to add ammonium hydroxide to a solution of $La(NO_3)_3 \cdot 6H_2O$ and, if present, a metal in the form of a water soluble compound, such as zinc nitrate. The ammonium hydroxide is added to the nitrate solution to a pH of about 8.8. At the end of the addition, the solution is filtered, the solid obtained is washed with water, and slowly heated to about 400° C., where it is calcined. The calcined product is then treated with a suitable vaporizable fluorine-containing compound as described above.

Compositions of this invention include catalytic compositions comprising at least one catalytic metal selected from the group consisting of chromium, cobalt, nickel, zinc and magnesium supported on a support of trivalent lanthanum compound containing fluoride anion wherein the atomic ratio of the catalytic metal(s) (i.e., total catalytic metal) to lanthanum is from about 1:1 to about 1:999. Of note are compositions where said catalytic metals are supported on lanthanum fluoride; and compositions where said catalytic metals are supported on fluorided lanthanum oxide. Preferably, the total catalytic metal content of these compositions is from aout 0.1 to 30 percent by weight, expressed as metal.

The vapor phase contacting with HF, in the presence of the catalysts of this invention, of the saturated or olefinic halogenated hydrocarbons of this invention of the formula $C_nH_aCl_bF_c$, wherein n is an integer from 1 to 6, a is an integer from 0 to to 12, b is an integer from 0 to 13 and c is an integer from 0 to 13, is typically conducted at about 150° C. to 500° C., preferably for saturated compounds at about 175° C. to 400° C., and more preferably for saturated compounds at about 200° C. to about 350° C., with a contact time of about 1 to about 120 seconds, preferably about 5 to about 60 seconds. The amount of HF ordinarily should be at least a stoichiometric amount. Typically, the molar ratio of HF to the said compounds of the formula $C_nH_aCl_bF_c$ can range from about 0.5:1 to about 100:1, preferably about 2:1 to 50:1, and more preferably about 3:1 to 10:1. In general, with a given catalyst composition, the higher the temperature and the longer the contact time, the greater is the conversion to fluorinated products. The above variables can be balanced, one against the other, so that the formation of higher fluorine substituted products is maximized.

Examples of olefinic compounds which may be reacted with HF in the presence of the catalysts of this invention include $CHCl=CCl_2$, $CCl_2=CCl_2$, $CCl_2=CClCCl_3$, $CCl_3CCl=CClCCl_3$, $CCl_2=CH_2$, $CHF=CF_2$, $CF_2=CH_2$ and $CF_2=CFCl$. Of note is a catalytic process for producing 2-chloro-1,1,1-trifluoroethane (HCFC-133a) by the fluorination of a trihaloethene of the formula $CX_2=CHCl$ wherein each X is chlorine or fluorine. Starting materials include trichloroethene, 1,2-dichlorofluoroethene and 1-chloro-2,2-difluoroethene. Trichloroethene is preferred. HCFC-133a is produced by reacting the above unsaturated compounds with HF in the vapor phase in the presence of the catalysts of this invention. The reaction of the above trihaloethenes with HF in the presence of the catalysts of the instant invention is preferably conducted at about 150° C. to 350° C., more preferably about 175° C. to 250° C. Oxygen may be added, if desired.

Also of note is a catalytic process for producing 2,2-dichloro-1,1,1-trifluoroethane ($CHCl_2CF_3$, i.e., HCFC-123), 1,1,1,2-tetrafluorochloroethane ($CHClFCF_3$, i.e., HCFC-124) and pentafluoroethane ($CHF_2CF_3$, i.e., HFC-125) by the fluorination of a tetrahaloethene of the formula $C_2Cl_{4-x}F_x$, wherein x equals 0 to 3 in the presence of the catalysts of this invention. Starting materials include $CCl_2=CCl_2$, $CClF=CCl_2$, $CClF=CClF$, $CF_2=CCl_2$ and $CF_2=CClF$. Tetrachloroethene is preferred. HCFC-123, HCFC-124 and/or HFC-125 are produced by reacting the above unsaturated compounds with HF in the vapor phase in the presence of the catalysts of this invention.

Examples of saturated compounds which may be reacted with HF in the presence of the catalysts of this invention include $CH_2Cl_2$, $CHCl_3$, $C_2Cl_6$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_5F$, $C_3H_2Cl_4F_2$, $C_3H_2Cl_3F_3$, $C_3H_2Cl_2F_4$, $C_3H_2ClF_5$ and $C_3H_2Cl_6$ (e.g., $CCl_3CH_2CCl_3$). Mixtures of saturated compounds may also be used (e.g., a mixture of $CH_2Cl_2$ and $CCl_3CF_3$; or a mixture of $CCl_2FCClF_2$ and $CCl_3CF_3$). Of note are catalytic processes for reacting 1,1,1-trichloro-2,2,2-trifluoroethane (i.e., $CCl_3CF_3$, CFC-113a), or reacting dichloromethane, with HF, in the vapor phase in the presence of the catalysts of this invention. For the reaction of CFC-113a with HF to yield $CCl_2FCF_3$ (CFC-114a), the $HF:CCl_3CF_3$ ratio can vary widely. The HF:CFC-113a molar ratio should be at least 0.5:1, but is preferably within the range of from about 2:1 to about 10:1.

For the reaction of dichloromethane to yield difluoromethane ($CH_2F_2$, HFC-32), the molar ratio of HF to $CH_2Cl_2$ preferred ranges are from about 1:1 to about 10:1. The reaction temperature normally ranges from about 180° C. to about 375° C. (e.g., from about 200° C. to about 350° C.).

For the reaction of mixtures of $CH_2Cl_2$ and $CCl_3CF_3$ to yield mixtures of $CH_2F_2$ and $CCl_2FCF_3$, the molar ratio of HF added to the total amount of $CH_2Cl_2$ and $CCl_3CF_3$ starting material typically ranges from about 0.5:1 to about 10:1, and is preferably from about 1:1 to 8:1. Typically, the molar ratio of $CH_2Cl_2$ to $CCl_3CF_3$ in mixtures ranges from 1:9 to about 9:1.

For the reaction of mixtures of $CCl_2FCClF_2$ and $CCl_3CF_3$ to yield mixtures of $CClF_2CClF_2$ and $CCl_2FCF_3$, the molar ratio of HF added to the total amount of $CCl_2FCClF_2$ and $CCl_3CF_3$ starting material typically ranges from about 1:1 to about 10:1, and is preferably from about 1:1 to 5:1. Typically, the molar ratio of $CCl_2FCClF_2$ to $CCl_3CF_3$ in mixtures ranges from 1:99 to about 9:1. The reaction of $C_2Cl_3F_3$ with HF in the presence of the catalysts of this invention can be used to obtain mixtures enriched in the asymmetric $C_2Cl_2F_4$ (i.e., $CCl_2FCF_3$) isomer.

Pressure is not critical. Atmospheric and superatmospheric pressures are the most convenient and are therefore preferred.

The reaction products are separated by conventional techniques, such as distillation. Some of the reaction products will have desired properties for commercial use. For example $CCl_3CF_3$ (CFC-113a) can be used to prepare CFC-114a which can then be converted to $CH_2FCF_3$ (HFC-134a) by hydrodechlorination.

The process of this invention can be calTied out readily in the vapor phase using well known chemical engineering practice.

The reaction zone and its associated feed lines, effluent lines and associated units should be constructed of materials resistant to hydrogen fluoride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

Preparation of Catalyst Precursors
Lanthanum Oxide Precursor for Catalyst A:

$La(NO_3)_3 \cdot 6H_2O$ (98.4 g) was dissolved in deionized water (1.5 L) in a 2 L beaker provided with an agitator. A solution (200 mL) of $NH_4OH$ and deionized water (1/1, volume/volume) was added during a period of 10 minutes to the agitated solution. The pH of the solution was 9.5 after this addition. The slurry was filtered and dried in air at 125° C. for about 18 hours, followed by calcination at 350° C. in air for an additional 8 hours. The product (46.8 g) was compressed into wafers and screened. Particles in the 12×20 mesh (1.4 mm×0.83 mm) range were used for the examples.
Lanthanum Oxide/Chromium Oxide Precursor for Catalyst B:

A solution of 195.2 g of $La(NO_3)_3 \cdot 6H_2O$ and 25.35 g $Cr(NO_3)_3 \cdot 9H_2O$ dissolved in 2.5 L deionized water was placed in a 4 L beaker provided with an agitator. To the stirred solution was added 260 mL of a solution prepared from 500 mL $NH_4H$ and 500 mL deionized water during a period of 15 minutes. The pH of the solution was 8.9 after this addition. The slurry was filtered and dried in air at 140° C. for 24 hours followed by calcination in air at 350° C. for an additional 8 hours. The solid was crushed and sieved. The fraction in the 10×30 mesh (2.0 mm×0.59 mm) range was used in the examples. The lanthanum to chromium weight ratio was nominally about 95:5.
Lanthanum Oxide/Chromium Oxide Precursor for Catalyst C:

Commercial lanthanum oxide (50 mL, 47.16 g) was washed several times with deionized water to remove fines. A solution of $Cr(NO_3)_3 \cdot 9H_2O$ (18.02 g) in deionized water (50 mL) was added to the wet lanthanum oxide in a 300 mL RB flask. The slurry was kept at room temperature for one hour with occasional stirring. The water was then removed using a rotary evaporator. The solid was dried overnight at about 120° C. and calcined at about 360° C. in air for about 24 hours. The dried catalyst precursor weighed 52.78 g. The granulated precursor (23.65 g, 20 mL) was activated according to the General Procedure for Preparation of Fluorinated Catalysts described below to prepare catalyst C. The lanthanum to chromium weight ratio was nominally about 95:5.
Lanthanum Oxide/Zinc Oxide Precursor for Catalyst D:

Commercial lanthanum oxide (50 mL, 46.70 g) was washed several times with deionized water to remove fines. A solution of $Zn(NO_3)_2 \cdot 6H_2O$ (4.21 g) in deionized water (50 mL) was added to the wet lanthanum oxide in a 300 mL RB flask. The slurry was kept at room temperature for one hour with occasional stirring. The water was then removed using a rotary evaporator. The solid was dried about 18 hours at about 100° C. and calcined at about 360° C. in air for about 18 hours. The dried catalyst precursor weighed 49.11 g. The granulated precursor (21.1 g, 20 mL) was activated according to the General Procedure for Preparation of Fluorinated Catalysts described below to prepare catalyst D. The lanthanum to zinc weight ratio was nominally about 98:2.
Lanthanum Oxide/Zinc Oxide/Chromium Oxide Precursor for Catalyst E:

Commercial lanthanum oxide (50 mL, 46.70 g) was washed several times with deionized water to remove fines. A solution of $Zn(NO_3)_2 \cdot 6H_2O$ (2.09 g) and $Cr(NO_3)_3 \cdot 9H_2O$ (3.55 g) in deionized water (50 mL) was added to the wet lanthanum oxide in a 300 mL RB flask. The slurry was kept at room temperature for one hour with occasional stilring. The water was then removed usino a rotary evaporator. The solid was dried about 18 hours at about 100° C. and calcincd at about 360° C. in air for about 24 hours. The dried catalyst precursor weighed 45.65 g. The granulated precursor (21.5 g, 20 mL) was activated according to the General Procedure for Preparation of Fluorinated Catalysts described below to prepare catalyst E. The lanthanum to zinc to chromium weight ratio was nominally about 98:1:1.
Lanthanum Oxide/Cobalt Oxide Precursor for Catalyst F:

Commercial lanthanum oxide (50 mL, 46.68 g) was washed several times with deionized water to remove fines. A solution of $Co(NO_3)_2 \cdot 6H_2O$ (18.02 g) in deionized water (50 mL) was added to the wet lanthanum oxide in a 300 mL RB flask. The slurry was kept at room temperature for one hour with occasional stiiring. The water was then removed using a rotary evaporator. The solid was dried about 18 hours at about 120° C. and calcined at about 360° C. in air for about 24 hours. The dried catalyst precursor weighed 47.88 g. The granulated precursor (21.0 g, 20 mL) was activated according to the General Procedure for Preparation of Fluorinated Catalysts described below to prepare catalyst F. The lanthanum to cobalt weight ratio was nominally about 98:2.
Aluminum Oxide/Chlromium Oxide Precursor for Catalyst G:

A solution made up of $Al(NO_3)_3 \cdot 9H_2O$ and $Cr(NO_3)_3 \cdot 9H_2O$ dissolved in deionized water was treated with $NH_4OH$ solution. The resulting slurry was then filtered. It was dried in air at 120° C. for about 18 hours followed by calcination in air at 350° C. for an additional 8 hours. The solid was pressed into disks, broken-up and sieved to provide a 10×30 mesh (2.0 mm×0.59 mm) fraction which was used in the examples. The aluminum to chromium weight ratio was nominally about 95:5.

General Procedure for the preparation of Fluorinated Catalysts

The granulated catalyst precursor (15 mL) was placed in a ⅝" (1.58 cm) Inconel® nickel alloy reactor heated in a fluidized sand bath. It was heated to 175° C. in a flow of nitrogen (50 cc/min) at which time HF flow (50 cc/min) was also started through the reactor. As the initial exotherm monitored by an internal thermocouple subsided (2–3 hours), nitrogen flow was decreased to 20 cc/min and HF flow increased to 80 cc/min. The reactor temperature was gradually increased to 400° C. during a 3–4 hour period and maintained at 400° C. for an additional 30 minutes. At the end of this period the reactor was brought to the desired operating temperature for catalyst evaluation. Catalyst A, Catalyst B, Catalyst C, Catalyst D, Catalyst E, Catalyst F and Catalyst G were prepared from their respective precursors using this general procedure.

Fluorination of commercial lanthanum oxide (Catalyst H)

A commercial sample of granulated lanthanum oxide (15 mL, 15.3 g) was charged in the reactor above. The lanthanum oxide was dried at 350° C. overnight prior to charging to the reactor. It was activated according to the General Procedure for Preparation of Fluorinated Catalysts described above. After activation, the weight of the fluorinated catalyst was 17.6 g.

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×⅛" (0.32 cm) diameter tubing containing Krytox® perfluorinated polyether on an inert carbon support. The helium flow was 35 mL/min. Gas chromatographic conditions were 70° C. for an initial hold period of three minutes followed by temperature programming to 180° C. at a rate of 6° C./minute. Unless indicated, the reported results are in mole %.

The bulk of the reactor effluent containing organic products and also inorganic acids such as HCl and HF was treated with aqueous caustic to neutralize the acids prior to disposal.

| Legend | |
| --- | --- |
| F115 is $CClF_2CF_3$ | F125 is $CHF_2CF_3$ |
| F114 is $CClF_2CClF_2$ | F124 is $CHClFCF_3$ |
| F114a is $CCl_2FCF_3$ | F124a is $CHF_2CClF_2$ |
| F113 is $CCl_2FCClF_2$ | F31 is $CH_2ClF$ |
| F113a is $CCl_3CF_3$ | F32 is $CH_2F_2$ |
| F133a is $CH_2ClCF_3$ | F123 is $CHCl_2CF_3$ |
| F134a is $CH_2FCF_3$ | F1122 is $CHF=CClF$ |
| F112/a is $CCl_2FCCl_2F + CCl_3CClF_2$ | |

Example 1

Fluorination of Dichloromethane

Catalyst B, 17.4 g, 15 cc $CH_2Cl_2 \rightarrow CH_2ClF + CH_2F_2$

The HF:dichloromethane molar ratio was 4:1 and the contact time was 15 seonds. Results at various temperatures are shown in the table.

| TEMP. ° C. | F32 | F31 | $CH_2Cl_2$ | OTHERS |
| --- | --- | --- | --- | --- |
| 150 | 1.1 | 8.7 | 90.0 | 0.2 |
| 175 | 5.1 | 16.9 | 77.8 | 0.2 |
| 200 | 19.1 | 19.7 | 60.9 | 0.1 |
| 225 | 55.4 | 11.8 | 32.7 | 0.1 |
| 250 | 60.6 | 12.0 | 27.3 | 0.1 |

Comparative Example A

Fluorination of Dichloromethane

Catalyst A, 20.5 g, 15 cc $CH_2Cl_2 \rightarrow CH_2ClF + CH_2F_2$

The HF:dichloromethane molar ratio was 4:1 and the contact time was 15 seconds. Results at various temperatures are shown in the table.

| TEMP. ° C. | F32 | F31 | $CH_2Cl_2$ |
| --- | --- | --- | --- |
| 200 | 1.2 | 9.8 | 89.0 |
| 225 | 6.2 | 20.7 | 73.1 |
| 250 | 12.8 | 23.0 | 64.2 |
| 275 | 31.8 | 19.8 | 48.5 |

Comparative Example B

Fluorination of Dichloromethane

Catalyst H, 17.6 g, 15 cc $CH_2Cl_2 \rightarrow CH_2ClF + CH_2F_2$

The HF:dichloromethane molar ratio was 4:1 and the contact time was 15 seconds. Results at various temperatures are shown in the table.

| TEMP. ° C. | F32 | F31 | $CH_2Cl_2$ |
| --- | --- | --- | --- |
| 250 | 0.4 | 5.5 | 93.7 |
| 275 | 2.2 | 10.7 | 86.7 |
| 300 | 10.2 | 16.9 | 72.6 |

Example 2

Fluorination of Dichloromethane

Catalyst C, 23.7 g, 20 cc $CH_2Cl_2 \rightarrow CH_2ClF + CH_2F_2$

The HF:dichloromethane molar ratio was 4:1 and the contact time was 15 seconds. After 3.5 hours, the following results were obtained at 225° C.; 59.2% F32, 10.9% F31 and 29.9% $CH_2Cl_2$.

Example 3

Fluorination of Dichloromethane

Catalyst D, 21.1 g, 20 cc $CH_2Cl_2 \rightarrow CH_2ClF + CH_2F_2$

The HF:dichloromethane molar ratio was 4:1 and the contact time was 15 seconds. Results at various temperatures are shown in the table.

| TEMP. °C. | F32 | F31 | $CH_2Cl_2$ |
|---|---|---|---|
| 225 | 4.3 | 15.8 | 79.9 |
| 250 | 24.5 | 18.1 | 57.4 |
| 275 | 19.7 | 19.0 | 61.3 |

Example 4

Fluorination of Dichloromethane
Catalyst E, 21.5 g, 20 cc
$CH_2Cl_2 \rightarrow CH_2ClF + CH_2F_2$
The HF:dichloromethane molar ratio was 4:1 and the contact time was 15 seconds. Results at various temperatures are shown in the table.

| TEMP. °C. | F32 | F31 | $CH_2Cl_2$ |
|---|---|---|---|
| 225 | 44.4 | 13.1 | 42.2 |
| 250 | 58.5 | 11.7 | 29.8 |

Example 5

Fluorination of Dichloromethane
Catalyst F, 21.0 g, 20 cc
$CH_2Cl_2 \rightarrow CH_2ClF + CH_2F_2$
The HF:dichloromethane molar ratio was 4:1 and the contact time was 15 seconds. Results at various temperatures are shown in the table.

| TEMP. °C. | F32 | F31 | $CH_2Cl_2$ |
|---|---|---|---|
| 225 | 7.9 | 18.1 | 74.0 |
| 250 | 28.6 | 19.7 | 51.7 |
| 275 | 45.2 | 15.6 | 39.2 |

Comparative Example C

Fluorination of Dichloromethane
Catalyst G, 14.2 g, 20 cc
$CH_2Cl_2 \rightarrow CH_2ClF + CH_2F_2$
The HF:dichloromethane molar ratio was 4:1 and the contact time was 15 seconds. Results at various temperatures are shown in the table.

| TEMP. °C. | F32 | F31 | $CH_2Cl_2$ |
|---|---|---|---|
| 175 | 1.5 | 13.3 | 85.0 |
| 200 | 2.0 | 13.0 | 84.7 |
| 225 | 1.9 | 12.7 | 85.0 |
| 250 | 20.2 | 17.2 | 62.1 |

Example 6

Fluorination of F113a
Catalyst B
$CCl_3CF_3 + HF \rightarrow CCl_2FCF_3$
The organic feed composition to the reactor was 98.6% F113a and 1.4% F114a. The HF:organic ratio was 2:1 and the contact time was 30 seconds. Results at various temperatures are shown in the table.

| TEMP. °C. | F115 | F114a | F113a | OTHERS |
|---|---|---|---|---|
| 250 | 0.0 | 20.9 | 78.9 | 0.1 |
| 275 | 0.0 | 29.3 | 70.6 | 0.1 |
| 300 | 0.1 | 66.6 | 33.2 | 0.1 |
| 325 | 0.5 | 93.1 | 6.3 | 0.1 |
| 350 | 1.5 | 92.9 | 5.4 | 0.2 |

Comparative Example D

Fluorination of F113a
Catalyst A
$CCl_3CF_3 + HF \rightarrow CCl_2FCF_3$
The organic feed composition to the reactor was 98.9% F113a, 0.8% F113 and 0.2% F114a. The HF:organic ratio was 2:1 and the contact time was 30 seconds. Results at various temperatures are shown in the table.

| TEMP. °C. | F114a | F113 | F113a |
|---|---|---|---|
| 275 | 1.3 | 0.3 | 98.4 |
| 300 | 5.7 | 0.2 | 94.0 |

Example 7

Fluorination of F113a
Catalyst C
$CCl_3CF_3 + HF \rightarrow CCl_2FCF_3$
The organic feed composition to the reactor was 98.9% F113a, 0.8% F113 and 0.2% F114a. The HF:organic ratio was 2:1 and the contact time was 30 seconds for all but the last entry in the table; for which it was 15 seconds. Results at various temperatures are shown in the table.

| TEMP. °C. | F114a | F113 | F113a |
|---|---|---|---|
| 250 | 16.6 | 0.2 | 82.8 |
| 275 | 39.0 | 0.2 | 60.7 |
| 300 | 82.7 | 0.2 | 16.1 |
| 300 | 65.2 | 0.2 | 34.2 |

Example 8

Fluorination of F113a
Catalyst D
$CCl_3CF_3 + HF \rightarrow CCl_2FCF_3$
The HF:organic ratio was 2:1 and the contact time was 30 seconds for all but the last entry in the table; for which it was 15 seconds. Results at various are shown in the table.

| TEMP. °C. | F114a | F113 | F113a |
|---|---|---|---|
| 275 | 2.4 | 0.2 | 97.4 |
| 300 | 4.5 | 0.2 | 95.3 |

Example 9

Fluorination of F113a

Catalyst E $CCl_3CF_3 + HF \rightarrow CCl_2FCF_3$

The HF:organic ratio was 2:1 and the contact time was 30 seconds. At 275° C. the following results were obtained; F114a, 24.2%, F113, 0.3% and F113a, 75.4%.

Example 10

Fluorination of F113a

Catalyst F $CCl_3CF_3 + HF \rightarrow CCl_2FCF_3$

The HF:organic ratio was 2:1. At 300° C. and a 15 second contact time, the folllowing results were obtained; F114a, 10.7%, F113, 0.2% and F113a, 89.1%. At 300° C. and a 30 second contact time, the following results were obtained; F114a, 19.1%, F113, 0.2% and F113a, 80.6%.

Comparative Example E

Fluorination of F113a

Catalyst G $CCl_3CF_3 + HF \rightarrow CCl_2FCF_3$

The organic feed composition to the reactor was 98.9% F113a, 0.8% F113 and 0.2% F114a. The HF:organic ratio was 2:1. Results at various temperatures are shown in the table. C.T. is the contact time in seconds.

| TEMP. ° C. | C.T. | F114a | F113a |
|---|---|---|---|
| 250 | 15 | 5.0 | 95.0 |
| 300 | 15 | 51.6 | 48.3 |
| 275 | 30 | 63.9 | 36.0 |
| 300 | 30 | 93.7 | 5.2 |

Example 11

Fluorination of F124a

Catalyst B $CHF_2CClF_2 + HF \rightarrow CHF_2CF_3$

The organic feed composition was 96.1% F124a and 3.4% F124. The HF:organic ratio was 4:1 and the contact time was 15 seconds. Results at various tempratures are shown in the table.

| TEMP. | F125 | F124a | F124 | OTHERS |
|---|---|---|---|---|
| 250 | 0.0 | 96.3 | 3.1 | 0.5 |
| 275 | 0.1 | 96.2 | 3.2 | 0.6 |
| 300 | 0.6 | 95.8 | 3.1 | 0.5 |
| 325 | 2.2 | 94.3 | 3.0 | 0.4 |
| 350 | 6.4 | 90.4 | 2.7 | 0.5 |

Example 12

Fluorination of F124

Catalyst B $CHClFCF_3 + HF \rightarrow CHF_2CF_3$

The organic feed composition was 96.9% F124, 0.7% F124a and 2.1% F134a. The HF:organic ratio was 4:1 and the contact time was 30 seconds. The products analyzed for the follwing, components (in mole %); F125, 14.0%; F134a, 2.0%; F124a, 0.9%; F124, 82.3%; F123, 0.6%; others, 0.3%

Example 13

Fluorination of F124

Catalyst C $CHClFCF_3 + HF \rightarrow CHF_2CF_3$

The organic feed composition was 99.8% F124 and 0.1% F124a. The HF:organic ratio was 4:1 and the contact time was 15 seconds. Results at various temperatures are shown in the table.

| TEMP. | F125 | F124 | F123 | OTHERS |
|---|---|---|---|---|
| 300 | 1.7 | 98.1 | 0.0 | 0.2 |
| 325 | 6.0 | 93.7 | 0.2 | 0.2 |
| 350 | 20.2 | 78.0 | 1.7 | 0.1 |

Example 14

Fluorination of F124

Catalyst D $CHClFCF_3 + HF \rightarrow CHF_2CF_3$

The organic feed composition was 99.8% F124 and 0.1% F124a. The HF:organic ratio was 4:1 and the contact time was 15 seconds. Results at various temperatures are shown in the table.

| TEMP. | F125 | F124 | OTHERS |
|---|---|---|---|
| 300 | 0.3 | 99.5 | 0.2 |
| 325 | 0.5 | 99.4 | 0.2 |
| 350 | 0.9 | 99.0 | 0.2 |

Example 15

Fluorination of F124

Catalyst F $CHClFCF_3 + HF \rightarrow CHF_2CF_3$

The organic feed composition was 99.8% F124 and 0.1% F124a. The HF:organic ratio was 4:1 and the contact time was 15 seconds. Results at various temperatures are shown in the table.

| TEMP. | F125 | F124 | OTHERS |
|---|---|---|---|
| 300 | 0.1 | 99.7 | 0.2 |
| 325 | 0.6 | 99.2 | 0.2 |
| 350 | 1.6 | 98.2 | 0.2 |

Comparative Example F

Fluorination of F124

Catalyst G $CHClFCF_3 + HF \rightarrow CHF_2CF_3$

The organic feed composition to the reactor was 99.8% F124 and 0.1% F124a. The HF:organic ratio was 4:1 and the contact time was 15 seconds. The operating temperature was 350° C. After about six hours of operation product analysis indicated 10.0% F125, and 88.8% F124 and small quantities of other products.

Example 16

Fluorination of F133a

Catalyst B $CH_2ClCF_3 + HF \rightarrow CH_2FCF_3$

The organic feed composition contained 98.9% F133a. 0.8% F114a and minor amounts of other products. The HF:organic ratio was 10:1 and the contact time was 10 seconds. Results at various temperatures are shown in the table.

| TEMP.° C. | F134a | F1122 | F124 | F133a | F114a | F123 |
|---|---|---|---|---|---|---|
| 350 | 7.2 | 0.1 | 0.1 | 91.7 | 0.8 | 0.1 |
| 370 | 15.6 | 0.1 | 0.1 | 82.9 | 0.9 | 0.2 |
| 390 | 25.1 | 0.3 | 0.1 | 72.9 | 0.8 | 0.4 |

Example 17

Fluorination of F113

Catalyst B $CCl_2FCClF_2 + HF \rightarrow CClF_2CClF_2$

The organic feed to the reactor was 99.8% F113 with small amounts of other products. The HF:organic ratio was 2:1 and the contact time was 30 seconds. Results at various temperatures are shown in the table.

| TEMP.° C. | F114 | F114a | F113 | F112/a | OTHERS |
|---|---|---|---|---|---|
| 350 | 9.5 | 0.7 | 89.6 | 0.1 | 0.0 |
| 375 | 31.3 | 1.3 | 66.8 | 0.4 | 0.2 |

Minor quantities of other products were present.

Example 18

Fluorination of F113/F113a mixture (50/50)

Catalyst B $C_2Cl_3F_3 + HF \rightarrow C_2Cl_2F_4$

The organic feed to the reactor contained 49.6% 113a and 50.1% 113. The HF:organic ratio was 2:1 and the contact time was 30 seconds. Results at various temperatures are shown in the table.

| TEMP.° C. | F115 | F114 | F114a | F113 | F113a | F112/a |
|---|---|---|---|---|---|---|
| 300 | 0.0 | 0.2 | 24.8 | 48.8 | 26.0 | 0.1 |
| 325 | 0.2 | 1.2 | 48.2 | 46.7 | 3.0 | 0.6 |
| 350 | 1.0 | 5.0 | 49.3 | 41.7 | 1.6 | 1.1 |
| 375 | 3.1 | 14.2 | 47.8 | 32.4 | 1.5 | 0.8 |

Small amounts of other products were present.

Example 19

Fluorination of F113/F113a mixture (75/25)

Catalyst B $C_2Cl_3F_3 + HF \rightarrow C_2Cl_2F_4$

The organic feed to the reactor contained 24.5% F113a and 75.4% F113. The HF:organic ratio was 2:1 and the contact time was 30 seconds. Results at various temperatures are shown in the table.

| TEMP.° C. | F115 | F114 | F114a | F113 | F113a | F112/a |
|---|---|---|---|---|---|---|
| 300 | 0.0 | 0.5 | 15.4 | 73.9 | 10.1 | 0.1 |
| 325 | 0.1 | 2.2 | 24.5 | 71.6 | 1.1 | 0.5 |
| 350 | 0.6 | 9.0 | 25.1 | 64.1 | 0.4 | 0.7 |

Example 20

Fluorination of F113a/CH₂Cl₂ (80/20)

Catalyst B

The composition of the feed in mole % is shown in the table. The HF:organic ratio was 4:1 and the contact time was 15 seconds. Results at various temperatures are shown in the table.

| TEMP.° C. | F32 | F31 | $CH_2Cl_2$ | F114a | F113 | F113a |
|---|---|---|---|---|---|---|
| FEED | 0.3 | 2.2 | 19.8 | 0.5 | 0.2 | 76.9 |
| 225 | 13.8 | 1.3 | 2.4 | 0.8 | 0.2 | 81.3 |
| 250 | 15.7 | 0.8 | 0.5 | 2.6 | 0.2 | 80.0 |
| 275 | 15.6 | 0.9 | 0.6 | 9.1 | 0.2 | 73.5 |
| 300 | 14.5 | 1.4 | 1.3 | 32.1 | 0.2 | 50.4 |

Example 21

Fluorination of F113a/CH₂Cl₂ (20/80)

Catalyst B

The composition of the feed in mole % is shown in the table. The HF:organic ratio was 4:1 and the contact time was 15 seconds. Results at various temperatures are shown in the table.

| TEMP.° C. | F32 | F31 | $CH_2Cl_2$ | F114a | F113 | F113a |
|---|---|---|---|---|---|---|
| FEED | 0.7 | 6.5 | 74.9 | 0.0 | 0.1 | 17.8 |
| 200 | 17.5 | 15.3 | 47.8 | 0.1 | 0.1 | 19.2 |
| 225 | 43.0 | 9.5 | 27.2 | 0.1 | 0.1 | 20.2 |
| 250 | 51.0 | 9.2 | 18.7 | 0.5 | 0.1 | 20.5 |
| 275 | 48.9 | 9.9 | 20.2 | 2.5 | 0.1 | 18.4 |
| 300 | 47.8 | 10.4 | 20.9 | 8.6 | 0.1 | 12.1 |
| 325 | 43.3 | 11.5 | 24.8 | 17.0 | 0.1 | 3.4 |

What is claimed is:

1. A catalytic composition comprising at least one catalytic metal selected from the group consisting of chromium, nickel, cobalt, zinc, and magnesium, supported on a support of trivalent lanthanum compound selected from the group consisting of lanthanum fluoride and fluorided lanthanum oxide consisting essentially of lanthanum, oxygen and fluorine present in such proportions that the fluorine content corresponds to a $LaF_3$ content of at least 80 weight percent of the catalyst exclusive of compounds of the supported catalytic metal; the atomic ratio of catalytic metal to lanthanum being from about 1:1 to about 1:999.

2. The composition of claim 2 wherein the total catalytic metal content of the catalyst is from about 0.05 to 50 percent by weight expressed as metal.

3. The composition of claim 1 wherein the total catalytic metal content is from about 0.1 to 30 percent by weight.

4. The composition of claim 1 wherein the catalytic metal is chromium.

5. The composition of claim 1 comprising chromium supported on fluorided lanthanum oxide.

6. The composition of claim 1 consisting essentially of chromium supported on fluorided lanthanum oxide.

7. The composition of claim 1 wherein catalytic metal is supported on lanthanum fluoride.

8. The composition of claim 1 wherein the catalytic metal is supported on fluorided lanthanum oxide.

9. A process for increasing the fluorine content of a saturated or olefinic starting material of the formula $C_nH_aCl_bF_c$, wherein n is an integer from 1 to 6, a is an integer from 0 to 12, b is an integer from 0 to 13 and c is an integer from 0 to 13, provided that said starting material is a halogenated hydrocarbon, characterized by:

contacting said starting material in the vapor phase at a temperature in the range of about 150° C. to about 500° C. with HF and a catalytic composition of claim 1.

10. The process of claim 9 wherein the total catalytic metal content of the catalyst is from about 0.05 to 50 percent by weight expressed as metal.

11. The process of claim 9 wherein the total catalytic metal content is from about 0.1 to 30 percent by weight.

12. The process of claim 9 wherein the catalytic metal is selected from the group consisting of chromium, cobalt, nickel, zinc, and magnesium.

13. The process of claim 9 wherein $CH_2Cl_2$ is contacted with HF and a catalyst of chromium supported on fluorided lanthanum oxide.

14. The process of claim 9 wherein $CCl_3CF_3$ is contacted with HF and a catalyst of chromium supported on fluorided lanthanum oxide.

15. A process for increasing the fluorine content of at least one halogenated hydrocarbon starting material selected from the group consisting of the olefinic compounds $CHCl=CClF$, $CHCl=CF_2$, $CHCl=CCl_2$, $CCl_2=CCl_2$, $CClF=CCl_2$, $CClF=CClF$, $CF_2=CCl_2$, $CCl_2=CClCCl_3$, $CCl_3CCl=CClCCl_3$, $CCl_2=CH_2$, $CHF=CF_2$, $CF_2=CH_2$ and $CF_2=CFCl$ and the saturated compounds $CH_2Cl2$, $CHCl_3$, $C_2Cl_6$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_3HCl_7$, $C_3HCl_6F$, $C_3HCl_5H_2$, $C_3HCl_4F_3$, $C_3HCl_3F_4$, $C_3HCl_2F_5$, $C_3H_2Cl_5F$, $C_3H_2Cl_4F_2$, $C_3H_2Cl_3F_3$, $C_3H_2Cl_2F_4$, $C_3H_2ClF_5$ and $C_3H_2Cl_6$, characterized by:

contacting said at least one starting material in the vapor phase at a temperature in the range of about 150° C. to about 500° C. with HF and a catalytic composition of claim 7.

* * * * *